(12) United States Patent
Papini et al.

(10) Patent No.: US 11,751,803 B2
(45) Date of Patent: Sep. 12, 2023

(54) SLEEP APNEA DETECTION SYSTEM AND METHOD

(71) Applicant: KONINKLIJKE PHILIPS N.V., Eindhoven (NL)

(72) Inventors: Gabriele Papini, Eindhoven (NL); Pedro Miguel Ferreira Dos Santos Da Fonesca, Borgerhout (BE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 139 days.

(21) Appl. No.: 17/190,471

(22) Filed: Mar. 3, 2021

(65) Prior Publication Data
US 2021/0275090 A1    Sep. 9, 2021

(30) Foreign Application Priority Data
Mar. 3, 2020 (EP) .................... 20160618

(51) Int. Cl.
A61B 5/00 (2006.01)
G16H 40/67 (2018.01)
(Continued)

(52) U.S. Cl.
CPC .......... A61B 5/4818 (2013.01); A61B 5/0205 (2013.01); A61B 5/02416 (2013.01);
(Continued)

(58) Field of Classification Search
CPC . A61B 5/4818; A61B 5/0205; A61B 5/02416; A61B 5/4812; A61B 5/7267;
(Continued)

(56) References Cited

U.S. PATENT DOCUMENTS 7,690,378 B1 * 4/2010 Turcott ................ A61B 5/4818
600/501
10,321,871 B2 * 6/2019 Bandyopadhyay .... G16H 50/20
(Continued)

FOREIGN PATENT DOCUMENTS

| EP | 3536225 A1 | 9/2019 | |
|----|-----------|--------|---|
| WO | 2006037184 A1 | 4/2006 | |
| WO | WO-2006037184 A1 * | 4/2006 | ........... A61B 5/0826 |

OTHER PUBLICATIONS

A, H. Khandoker et al: "Investigating Relative Respiratory Effort Signals During Mixed Sleep Apnea Using Photoplethysmogram", Annals of Biomedical Engineering, vol. 41, No. 10, May 22, 2013 (May 22, 2013) p. 2229-2236, XP55702822, NY, ISSN:0090-6964, DOI:10.1007/S10439-013-0827-1 (Year: 2013).*
(Continued)

Primary Examiner — Carl H Layno
Assistant Examiner — Michael J Lau

(57) ABSTRACT

A system for detecting sleep apnea uses a PPG sensor for generating a PPG signal. An estimate of respiratory effort is derived from the PPG signal, and from this a respiratory effort signal is derived. Characteristic features are extracted from the respiratory effort signal, and sleep disordered breathing events are detected from the extracted characteristic features. This analysis can distinguish between sleep disordered breathing events and normal breathing during sleep.

15 Claims, 4 Drawing Sheets

(51) Int. Cl.
*G16H 50/30* (2018.01)
*A61B 5/0205* (2006.01)
*A61B 5/024* (2006.01)
*A61B 5/08* (2006.01)

(52) U.S. Cl.
CPC .......... *A61B 5/4812* (2013.01); *A61B 5/7267* (2013.01); *A61B 5/7278* (2013.01); *A61B 5/7282* (2013.01); *G16H 40/67* (2018.01); *G16H 50/30* (2018.01); *A61B 5/02405* (2013.01); *A61B 5/0816* (2013.01); *A61B 2562/0219* (2013.01)

(58) Field of Classification Search
CPC . A61B 5/7278; A61B 5/7282; A61B 5/02405; A61B 2562/0219; G16H 50/30; G16H 40/67
USPC .......................................................... 600/301
See application file for complete search history.

(56) References Cited

U.S. PATENT DOCUMENTS

| | | | |
|---|---|---|---|
| 2010/0121207 | A1 | 5/2010 | Moersdorf |
| 2015/0164375 | A1* | 6/2015 | Schindhelm ........... A61B 5/113 600/534 |
| 2016/0338597 | A1* | 11/2016 | Melker .................. A61B 5/746 |
| 2020/0093422 | A1* | 3/2020 | Ferreira Dos Santos Da Fonseca ............... A61B 5/0205 |

OTHER PUBLICATIONS

Jayawardhana Madhuka et al: Enhanced detection of sleep apnoea using heart-rate, respiration effort, and oxygen saturation derived from a photoplethysmography sensor, 2017 39th Annual international conference of the IEEE engineering in medicine and biology society (EMBC), IEEE, Jul. 11, 2017. (Year: 2017).*

"Investigating Relative Respiratory Effort Signals During Mixed Sleep Apnea Using Photoplethysmogram" of A. Khandoker et. al., Annals of Biomedical Engineering, vol. 41, No. 10, May 11, 2013 pp. 2229-2236.

"Enhanced detection of sleep apnoea using heart-rate, respiration effort and oxygen saturation derived from a photoplethysmography sensor" of J. Madhuka et. al., 2017 39th Annual Conference of the IEEE Engineering in Medicine and Biology Society, Jul. 11, 2017, pp. 121-124.

Hall, Mark A. 1999. "Correlation-Based Feature Selection for Machine Learning." The University of Waikato.

Papini, Gabriele B., et al. "Sinus or not: a new beat detection algorithm based on a pulse morphology quality index to extract normal sinus rhythm beats from wrist-worn photoplethysmography recordings." Physiological measurement 39.11 (2018): 115007).

Fonseca, Pedro, Xi Long, Mustafa Radha, Reinder Haakma, Ronald M Aarts, and Jérôme Rolink. 2015. "Sleep Stage Classification with ECG and Respiratory Effort." IOP Physiological Measurement 36: 2027-40.

X. Long et al. "Analyzing respiratory effort amplitude for automated sleep stage classification," Biomed. Signal Process. Control, vol. 14, pp. 197:205, 2014.).

C. Karmakar et al. "Detection of Respiratory Arousals Using Photoplethysmography (PPG) Signal in Sleep Apnea Patients," IEEE Journal of Biomedical and Health Informatics, vol. 18, No. 3, pp. 1065-1073, 2014.

Lévy, P. et al. Obstructive sleep apnoea syndrome. Nat. Rev. Dis. Primers 2015, 1, 15015.

Mendonça, F., Mostafa, S. S., Ravelo-García, A. G., Morgado-Dias, F. & Penzel, T. A review of obstructive sleep apnea detection approaches. IEEE J. Biomed. Heal. Informatics 2018, 1-1.

Allen J. Photoplethysmography and its application in clinical physiological measurement. Physiol Meas. 2007; 28(3): R1-R39.

Spierer DK, Rosen Z, Litman LL, Fujii K. Validation of photoplethysmography as a method to detect heart rate during rest and exercise. J Med Eng Technol. 2015;39(5):264-271.

Charlton P.H. et al. An assessment of algorithms to estimate respiratory rate from the electrocardiogram and photoplethysmogram. Physiol. Meas. 2016; 37 610.

Ravelo-García, Antonio G., et al. "An approach to the enhancement of sleep apnea detection by means of detrended fluctuation analysis of RR intervals." Computing in Cardiology 2014. IEEE, 2014.

Papini, G. B. et al. On the generalizability of ECG-based obstructive sleep apnea monitoring: merits and limitations of the Apnea-ECG database. In 2018 40th Annual International Conference of the IEEE Engineering in Medicine and Biology Society (EMBC), 6022-6025, (2018).

* cited by examiner

SLEEP APNEA DETECTION SYSTEM AND METHOD

FIELD OF THE INVENTION

This invention relates to the detection of sleep apnea, where apnea is used as a general term to include sleep breathing disorders characterized by occurrence of sleep disordered breathing events such as obstructive sleep apnea, central sleep apnea but also hypopnea and mixed apnea episodes.

BACKGROUND OF THE INVENTION

Sleep apnea is a general term used to designate two types of sleep breathing disorders, namely obstructive sleep apnea (OSA) and central sleep apnea (CSA). Although they are caused by different physiological phenomena, they are both associated with reductions (hypopneas) or complete cessations (apneas) in airflow, leading to a decrease in blood oxygen saturation, and an eventual cortical arousal and associated burst in sympathetic activity with an accompanied increase in heart rate and blood pressure.

OSA and CSA refer to breathing disorders. OSA is characterized by a repetitive occurrence of obstructive apnea events, but also (obstructive) hypopnea events. Sometimes central apnea events are also taken into account for OSA disorder. Similarly CSA is characterized by repetitive central apnea events and also hypopnea events. Apnea and hypopnea events are the individual instances of cessation (apnea) or reduction (hypopnea) in air flow. The term 'sleep disordered breathing event' (SDB event) is typically used as a general term to refer to an apnea event or hypopnea event or a respiratory-related arousal event.

Repetitive apnea and hypopnea events interrupt sleep continuity and reduce sleep time, which partly explains one of the defining symptoms: excessive daytime sleepiness. Sleep apnea has been associated with an increased risk of cardiac and cerebrovascular diseases such as hypertension, heart failure, arrhythmias, myocardial ischemia and infarction, pulmonary arterial hypertension, renal disease, metabolic dysregulation, insulin resistance and lipid disorders, stroke, dementia and cognitive impairment in the elderly, and changes in cerebral blood flow and cerebral autoregulation. Therefore, early and simplified diagnoses of sleep apnea using a limited number of sensor sources is desirable.

OSA is the most common type of sleep breathing disorder and is caused by a complete or partial obstruction of the upper airway. Normally during sleep, muscles in the tongue, mouth and pharynx relax slightly but not enough to obstruct the airway. In the case of OSA, the muscles are relaxed too much. The tongue presses against the back of the upper airway obstructing the airflow towards the lungs.

During an obstructive apnea or hypopnea event, the heart rate decreases and the blood oxygen saturation reduces. When the brain does not get sufficient oxygen, because of the resistance to airflow, the obstruction may lead to arousals where the subject will partially or fully wake up from a sleep state. Usually, the subject gasps for air to re-establish airflow before returning to a sleep state. This is a cyclic pattern, which usually repeats (often more than 100 times) throughout the night. Apnea and hypopnea episodes last typically between 20s and 40s.

Although less common than OSA, CSA is nonetheless a relevant sleep breathing disorder, more often seen in patients suffering from other comorbidities, such as heart failure and neurological conditions. Central apnea events are characterized by a cessation of airflow and also respiratory effort (central apnea), or a reduction in airflow and respiratory effort without clear evidence of partially obstructed breathing (central hypopnea).

In order to quantify the severity of a sleep disordered breathing condition, an index comprising both central and obstructive apneas and hypopneas is used. The apnea-hypopnea index (AHI) reflects the average number of apneas and/or hypopneas per hour of observed sleep. In adults, an AHI≤5 is considered to be normal. Mild apnea is characterized by an AHI between 5-15 events per hour, moderate apnea between 15-30 events per hour, and severe apnea is associated with an AHI value greater than 30 events per hour. Often people are not aware of the frequent awakenings during the night.

Regarding apnea prevalence, AHI≥5 in adults between 30-60 years is about 9% for females and 24% for males. Obesity is the strongest risk factor for apnea and is reflected by several parameters including body mass index, neck circumference, and waist-to-hip ratio. Other risk factors include aging, gender, loss of muscle tone in pharynx, swollen tonsils, menopause, upper airway anatomy, smoking cigarettes, alcohol, ethnicity and the presence of other cardiac or neurological conditions. There seems to be a direct relationship between the apnea epidemic and the obesity epidemic.

There are many signs associated with apnea such as loud snoring, frequent awakenings from sleep gasping for air to restore airflow, or having a feeling of choking. People having apnea predominantly experience excessive daytime sleepiness or fatigue. Other complaints are related to insomnia and depressions. Fragmented sleep due to apnea may cause a poorer daytime cognitive performance, increased risk vehicle and workplace accidents.

Sleep apnea can be treated by applying continuous positive airway pressure (CPAP) through the nose by means of a mask that the patient has to wear during the night. The traditional practice of diagnosing sleep apnea is that patients are monitored during a sleep study. Sleep studies are expensive and require overnight polysomnography (PSG) evaluation in sleep laboratories as well as attending personal. A polysomnogram will typically record multiple parameters including:

Electroencephalogram (EEG) for monitoring brain activity;

Electrooculogram (EOG) to monitor eye movement;

Electromyogram (EMG) to monitor muscle tension;

Electrocardiogram (ECG) to monitor the electric activity of the heart;

Respiratory inductance plethysmography or piezoelectric belts around the thorax and abdomen to measure respiratory effort;

Nasal and oral thermistors or pressure sensors to measure airflow; and

Pulse oximetry to monitor changes in blood oxygen levels.

Because of the limited availability of sleep laboratories and the high costs associated with sleep studies, underdiagnosis of sleep apnea is a large problem. It is reported that about 80%-85% of the people with OSA are under-diagnosed.

Simplified polygraphic measurements, such as those used in home sleep tests, can be used to measure and diagnose sleep disordered breathing at home. However, these arrangements, albeit less complex than PSG, are still cumbersome, relatively uncomfortable, and cannot, practically, be used for more than one or two nights.

In the last two decades, several algorithms have been proposed to enable objective OSA monitoring without incurring the costs and obtrusiveness of PSG and similar methods.

There are for example known algorithms to detect apnea and hypopnea episodes based on heart rate variability (HRV) features extracted from an ECG signal and/or a photoplethysmography (PPG) signal. An apnea/hypopnea episode has a significant impact on the instantaneous heart rate and hemodynamics. These episodes result in a recurring heart rate pattern, called cyclic variation of heart rate (CVHR). CVHR peaks are due to abrupt increases in heart rate during the arousal phase that terminates the apnea or hypopnea event. Modern wearable devices, such as wrist-worn reflective PPG sensor, are easily accepted by users, many of whom are currently using them to monitor their own sleep.

The features extracted from the cardiovascular ECG or PPG signals can be indirectly related to the presence of sleep events related to OSA.

In addition to cardiovascular information, respiratory effort is an important parameter to monitor OSA because it is directly related to the sleep disordered breathing (SDB) events: obstructive apnea and hypopnea consist of complete or partial obstructions of the upper airway and, therefore, they generate an increase in respiratory effort.

One possible approach to take account of respiratory effort is to measure body movements with an accelerometer. This movement information can then be combined with the HRV information measured with a PPG sensor, to monitor OSA. For instance such an approach can be used for OSA screening, to detect an epoch containing SDB events, and to determine the average number of events (apnea or hypopnea) per hour (i.e. apnea-hypopnea index, AHI).

WO 2006/037184 discloses the measurement of flow to detect disordered breathing events, and uses a measure of respiratory effort from a PPG signal to distinguish between the type of disordered breathing event. The flow is directly measured by CPAP flow meters or pressure sensors. A pulse oximeter is also used to provide oxygen saturation information in order to detect desaturations, associated with the occurrence of disordered breathing events.

The article "Investigating Relative Respiratory Effort Signals During Mixed Sleep Apnea Using Photoplethysmogram" of A. Khandoker et. al., Annals of Biomedical Engineering, vol. 41, no. 10, 11 May 2013 pp. 2229-2236 discloses the use of a respiratory effort signal obtained by a PPG sensor to distinguish apnea characteristics.

The article "Enhanced detection of sleep apnoea using heart-rate, respiration effort and oxygen saturation derived from a photoplethysmography sensor" of J. Madhuka et. al., 2017 39th Annual Conference of the IEEE Engineering in Medicine and Biology Society, 11 Jul. 2017, pp. 121-124 discloses the use of heart-rate, respiratory effort and oxygen saturation to detect sleep apnea.

It would be desirable to enable respiratory effort to be taken into account in the detection of sleep apnea events but with a reduced complexity of the required sensing arrangement.

SUMMARY OF THE INVENTION

The invention is defined by the claims.

According to examples in accordance with an aspect of the invention, there is provided a system for detecting sleep apnea, comprising:

a PPG sensor for generating a PPG signal for use in detecting sleep apnea; and a processor, which is adapted to:

provide an estimate of respiratory effort from the PPG signal and thereby derive a respiratory effort signal;

extract characteristic features from the respiratory effort signal; and detect sleep disordered breathing events from the extracted characteristic features and thereby distinguish between sleep disordered breathing events and normal breathing during sleep.

The general term 'sleep disordered breathing events' (SDB events) is a term of the art and refers to any apnea or hypopnea event. It may also cover respiratory-related arousal events. Thus, the expression sleep disordered breathing event may be used in this disclosure interchangeably with reference to an apnea or hypopnea event. Embodiments of the invention are for detecting both apnea events and hypopnea events as a means of identifying sleep breathing disorders.

The system of the invention derives a surrogate measure (an estimate) of respiratory effort from a PPG signal. Respiratory features can then be computed based on this respiratory effort signal, and can then be used to monitor sleep apnea and hypopnea events, and in particular distinguish between sleep disordered breathing events (obstructive or central apneas or hypopneas) and normal sleep. Despite the fact that the measure of surrogate respiratory effort does not always correlate well with the conventional reference respiratory effort signal as would be measured with a respiratory belt, for example, the surrogate signal does exhibit different and identifiable characteristic features when sleep disordered breathing events are happening. Thus, it enables these characteristic features to be used to improve the performance of an algorithm for apnea monitoring.

By using a PPG signal to obtain a surrogate respiratory effort signal, the system does not require airflow sensing (e.g. using pressure sensors or airflow sensors). Thus the analysis of a PPG signal alone enables the system to distinguish between sleep disordered breathing events and normal breathing during sleep. Furthermore, a single wavelength PPG signal is preferably used, namely a signal from a single wavelength PPG sensor (rather than a multi-wavelength pulse oximeter), or else a single channel is processed from a multiple wavelength PPG sensor, so enabling a low cost system in terms of the hardware and/or the signal processing.

The processor is for example adapted to identify epoch periods during which sleep disordered breathing events are detected. These epoch periods may then be used for generating apnea report information.

The processor is for example adapted to provide an estimate of respiratory effort by one or more of:

determining the amplitude of pulses in the PPG signal;

determining the distance between PPG pulses; and determining the envelope of the peaks of the PPG pulses.

Various different PPG signal characteristics may be used to derive the respiratory effort signal. As explained above, it does not need to match any particular known respiratory signal format, as long as it encodes features which relate to the respiratory cycle and effort.

The processor may be adapted to extract characteristic features by determining the signal power at the respiration frequency. This one measure of the respiratory effort signal which may be used to detect the sleep disordered breathing events.

The processor may be further adapted to extract cardiac features from the PPG signal.

It is known to use cardiac features from a PPG signal to detect apnea events. By combining this known information with the estimated respiratory effort signal, the apnea event detection is made more accurate and reliable.

The processor may be adapted to extract cardiac features by one or more of:
  determining the average heart beat interval;
  determining a standard deviation of a heart beat interval;
  determining a range of the heart beat interval; and
  determining the nth percentile of the heart beat interval.

Thus, various cardiac features may be used as part of the detection of apnea or hypopnea events.

The processor may be adapted (additionally or alternatively) to extract cardiac features by performing power spectral density analysis. Thus, the way signal power is distributed over different frequency bands may be influenced with apnea or hypopnea events.

The processor may be further adapted to extract cardiorespiratory coupling features from the PPG signal. It is known that the interaction between cardiac and respiratory activity varies across sleep stages, and it is also found that variations exist between epochs with and without sleep disordered breathing events. Thus, cardiorespiratory information may further be used to increase the accuracy of sleep disordered breathing event detection.

The processor may be further adapted to derive sleep stages from heart rate variability information derived from the PPG signal. The sleep stage information may also be taken into account when detecting sleep disordered breathing events. For example, WO 2019/170734 discloses the use of different sleep apnea detection algorithms for different sleep stages. However, sleep stage detection may be used instead simply to discriminate between awake and asleep periods.

The processor may be further adapted to derive an estimated apnea-hypopnea index value based on a total sleep time obtained from the sleep stages and identified epoch periods during which sleep disordered breathing events are detected.

The processor may also be adapted to determine a severity level of the detected sleep disordered breathing events. This may be achieved by applying thresholds to the determined apnea-hypopnea index value.

The system may further comprise an accelerometer for measuring body movements, wherein the processor is adapted to detect sleep disordered breathing events additionally taking account of body movements. This enables further refinement of the detection process.

In all examples, the processor may be adapted to extract features by using a trained neural network.

The invention also provides a computer-implemented method for detecting sleep apnea, comprising:
  receiving a PPG signal;
  providing an estimate of respiratory effort from the PPG signal and thereby deriving a respiratory effort signal;
  extracting characteristic features from the respiratory effort signal; and
  detecting sleep disordered breathing events from the extracted characteristic features.

The invention may be implemented at least in part in software.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
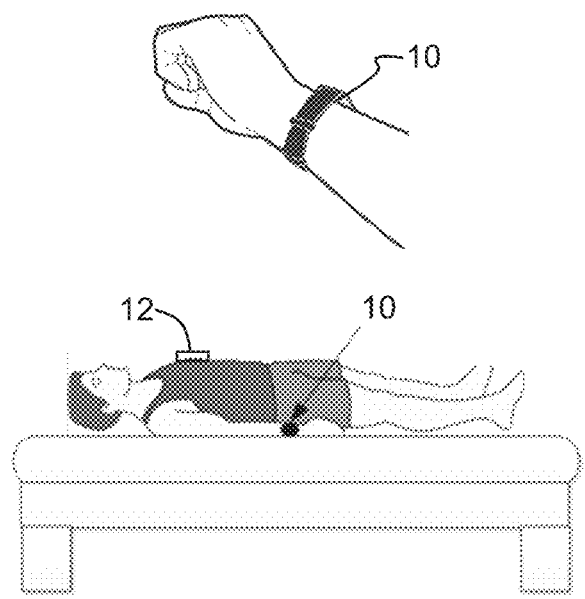
FIG. 1 shows a sleeping subject being monitored.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system for detecting sleep apnea which uses a PPG sensor for generating a PPG signal. An estimate of respiratory effort is derived from the PPG signal, and from this, a respiratory effort signal is derived. Characteristic features are extracted from the respiratory effort signal, and sleep apnea and hypopnea events are detected from the extracted characteristic features. This analysis can distinguish between sleep apnea/hypopnea events and normal breathing during sleep.

As discussed above, the general phrase 'sleep disordered breathing events' (SDB events) is used in the art to cover both apnea events and hypopnea events or also in some cases respiratory-related arousal events. Sometimes, simply the expression 'apnea event' can be used as shorthand for sleep disordered breathing events in general. In this disclosure, the term sleep disordered breathing event may therefore be used interchangeably with reference to apnea and hypopnea events, and reference herein to detection only of apnea events should be understood as compatible with detection also of hypopnea events.

FIG. 1 shows a sleeping subject. During sleep, the subject is monitored using a PPG sensor, and optionally also an accelerometer 12. The PPG sensor is shown as a wrist worn device, and the accelerometer is shown separate. They may however both be part of a single wrist worn sensor system. In further non-limiting examples, the PPG sensor may be a finger-worn PPG sensor (e.g. finger clip), or a forehead-mounted PPG sensor (e.g. adhered to head, or held with a head-band). In each case, an accelerometer can optionally be mounted together with the PPG sensor for measuring the relevant body movements.

Figure 2:
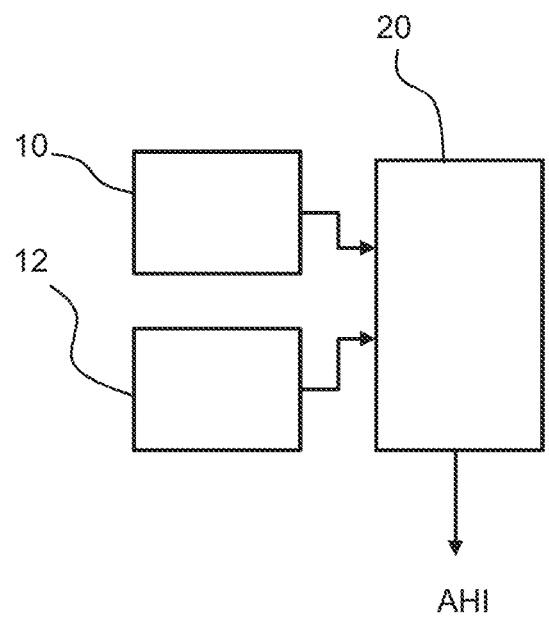
FIG. 2 shows an overall monitoring system.

FIG. 2 shows the overall system, in which a processor 20 receives the PPG signal, and optionally also the accelerometer signal, and detects sleep apnea or hypopnea events, for example to derive an apnea-hypopnea index (AHI).

One possible implementation of a PPG sensor is a pulse oximeter. While the purpose of such a sensor is to obtain a measure of blood oxygen saturation, it also detects changes in blood volume in the skin, and thereby performs PPG sensing. By detecting changes in blood volume, a cyclic signal corresponding to the pulse is obtained. PPG sensors, such as pulse oximeters, are thus commonly used to provide a measure of the pulse rate.

A PPG sensor contains at least one LED, and one light sensor. The LED and sensor are placed such that the LED directs light into the skin of the user, which is reflected or transmitted, and detected by the sensor. The amount of reflected/transmitted light is determined by, amongst others, the perfusion of blood within the skin.

The PPG system for example includes a red LED, a near-infrared LED, and a photodetector diode. The sensor is typically configured with the LEDs and photodetector diode directly on the skin of the subject.

The LEDs emit light at different wavelengths, which light is diffused through the vascular bed of the skin and received by the photodetector diode. The changing absorbance at each of the wavelengths is measured, allowing the sensor to determine the absorbance due to the pulsing arterial blood alone, excluding venous blood, skin, bone, muscle, and fat for example. The resulting PPG signal may then be analyzed.

Other simpler versions of a system for obtaining PPG data may be used, including a version with a single light source of one or more wavelengths. The absorption or reflectance of the light is modulated by the pulsatile arterial blood volume and detected using a photodetector device. A single wavelength PPG sensor instead does not provide oxygen saturation information. A single wavelength PPG signal may thus be obtained from a single wavelength PPG sensor or it may be a single wavelength channel from a multi-wavelength PPG sensor.

In transmissive pulse oximetry or basic PPG sensing, a sensor device is placed on a thin part of the body of the subject. Reflectance pulse oximetry or basic PPG sensing may be used as an alternative to transmissive pulse oximetry. This method does not require a thin section of the person's body and is therefore well suited to more universal application such as the wrist as shown above.

A basic design of a PPG sensor for example is a contact sensor with a single wavelength light source, e.g. green light (550 nm) to measure the PPG signal. The light source is pulsed with a certain light output frequency such as 128 Hz. A sampling frequency of the optical sensor is higher, for example 256 Hz so that it measures during light source activation and between light source activations. This allows the system to distinguish between the emitted light from the LED and the ambient light, and thereby filter out the ambient light from the signal received during a light source pulse.

In other known proposals, PPG data can be obtained from camera images, where ambient light and/or additional light sources are used to illuminate the tissue, such as skin. PPG measurements can thus even be carried out at a distance from the tissue, where the light source and/or detector are not in contact with the tissue, such as in the case of camera-based measurements.

The PPG data may be obtained at one or more wavelengths, such as any number of wavelengths typically between 1 and 10, but more than 10 wavelengths may even be used.

Apparatus and techniques for obtaining PPG data are well known in the art and indeed many different PPG sensors are commercially available. They are for example used in devices for measuring the heart rate during exercise.

It is well known that features of interest of the PPG signal relate to the heart rate variability (HRV). For this purpose, the beat onset of each cardiac cycle can be localized in the PPG signal. Noise-robust estimation of the inter-beat interval (IBI) time series can then be obtained, and HRV features can then be derived from the extracted IBI time series. This is a known process for the purpose of sleep stage detection and apnea detection.

Features extracted for heart rate variability determination can be grouped into the following categories:
Time domain linear features;
Frequency band power features;
Non-linear features describing irregularity of the inter-beat time interval (IBI) series;
Hilbert transform and Discrete Wavelet Transform features.

However, since the pulsatile component of the PPG mainly reflects heart rate activity, respiratory effort—based on which respiratory features can be extracted—is not immediately available.

The invention uses the PPG signal to derive an estimate (or surrogate) of respiratory effort so that respiratory effort signal is derived. Characteristic features are extracted from the respiratory effort signal, and sleep disordered breathing events (apnea events and hypopnea events) are detected from the extracted characteristic features. This analysis can distinguish between sleep disordered breathing events and normal breathing during sleep.

These characteristic respiratory features may optionally be used with the body movement information from the accelerometer and/or the HRV characteristics derived in known manner from the PPG signal, to monitor sleep disordered breathing events, including both OSA and CSA events.

Counter-intuitively, despite the fact that the measure of surrogate respiratory effort does not always correlate well with a conventional measure of respiratory effort, the surrogate signal has been found to exhibit different characteristics when sleep disordered breathing (obstructive and central apnea and hypopnea) events are happening, which allow these features to be used improve the performance of existing algorithms for apnea monitoring.

Figure 3:
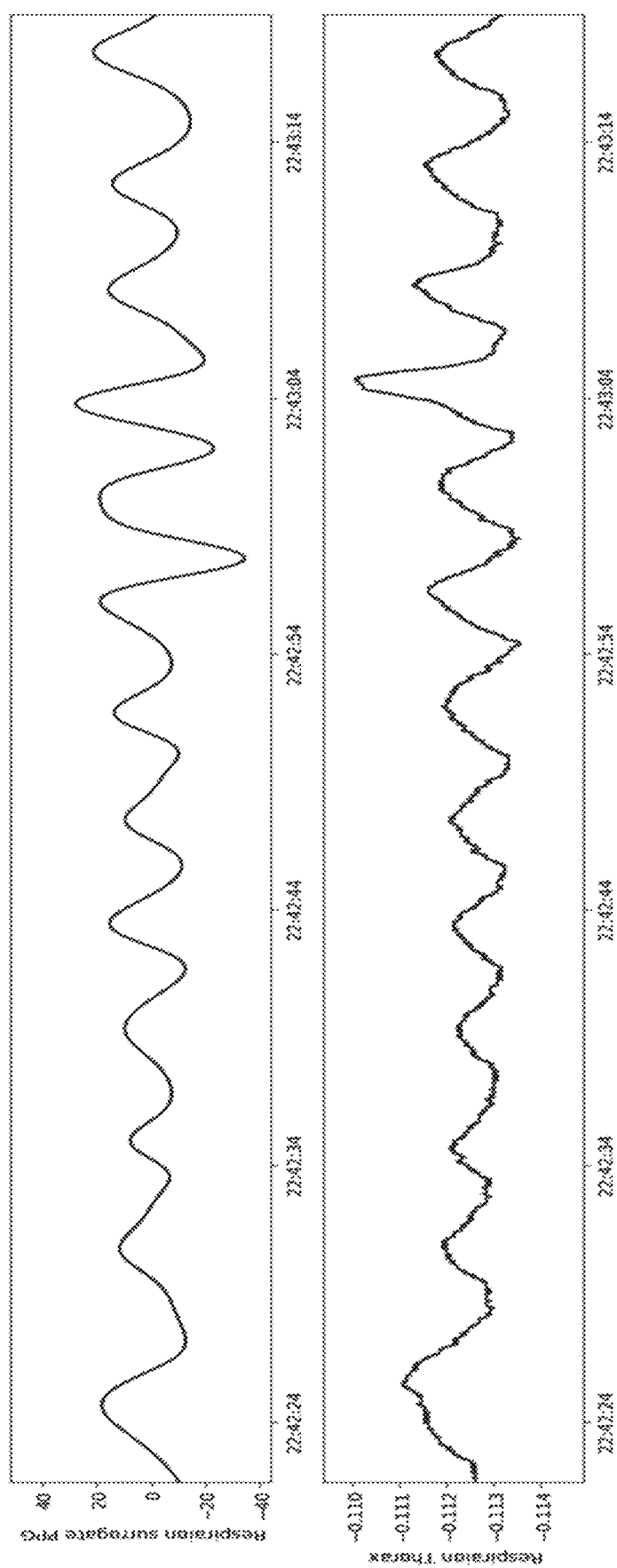
FIGS. 3 and 4 each show in the top plot a surrogate respiration signal derived from the PPG signal and in the bottom plot a respiration signal obtained from a thorax belt.

FIG. 3 shows in the top plot a surrogate respiration signal derived from the PPG signal. The bottom plot shows the respiration signal obtained from a thorax belt. FIG. 3 shows a close match between the signals.

Figure 4:
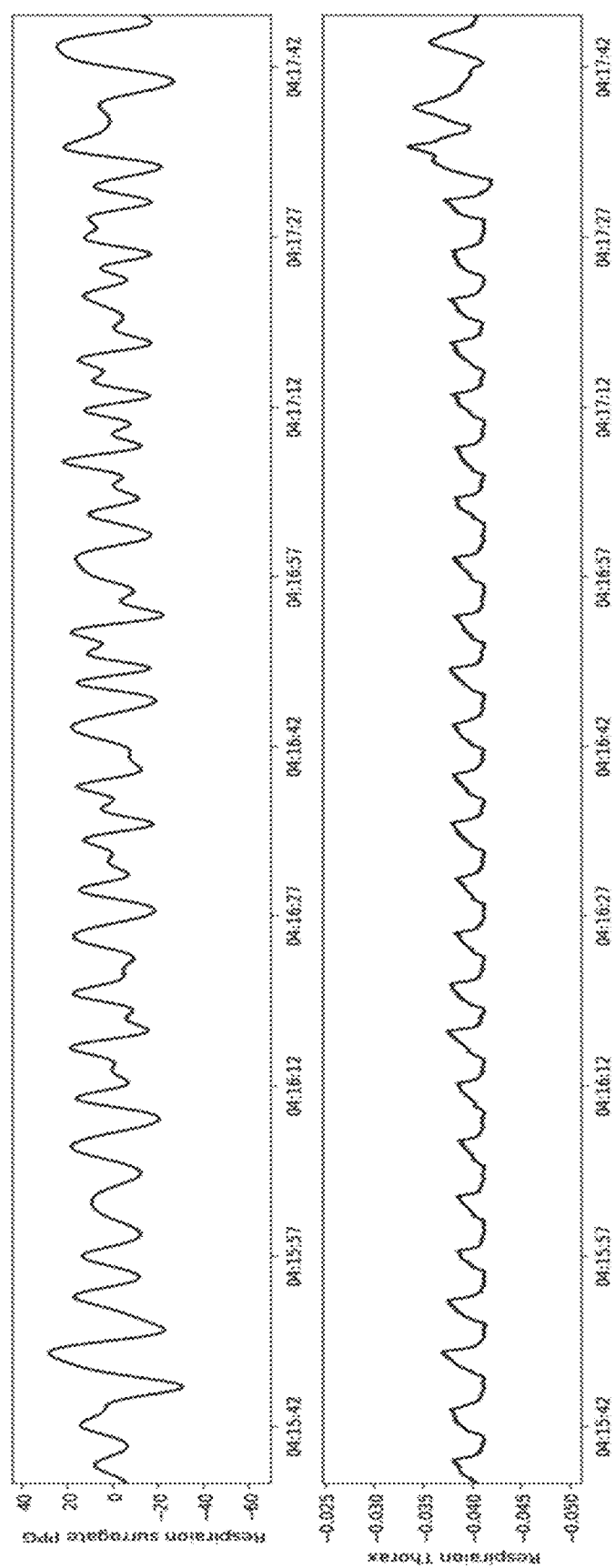

However, the signals will not always be a close match. FIG. 4 also shows in the top plot a surrogate respiration signal derived from the PPG signal and the bottom plot shows the respiration signal obtained from a thorax belt. Some respiration behavior can be seen in the PPG surrogate signal, but there are clear differences.

For instance, a closer match between the signals typically occurs during non-REM 3 sleep stage due to substantial coupling between cardiac and respiratory activity, lack of body movements, and lower sympathetic activity than in other non-REM sleep stages. The difference between the signals will typically increase during non-REM 1 sleep stage due to the higher sympathetic activity and higher likelihood of body movements compared to the other sleep stages. The constant sympathetic and parasympathetic oscillations occurring during REM may further contribute to a greater mismatch between the two signals.

Despite these possible differences, it has been found that the feature extraction from the surrogate respiration effort signal enables detection of sleep disordered breathing events. Thus, although a surrogate measure of respiratory effort correlates poorly with the signal measured with a belt worn around the thorax, extracted features are available which are statistically different in most of subject when an sleep disordered breathing event is present.

For example, the power at the respiration frequency calculated with the PPG-based respiration surrogate has a low correlation with the same features calculated with the reference thorax belt signal (average 0.15±0.22). However, this surrogate feature value is statistically different between epochs containing the end of a sleep disordered breathing event and those not containing such events in over 75% of the recordings (alpha<0.05 using the Mann-Whitney test).

Figure 5:
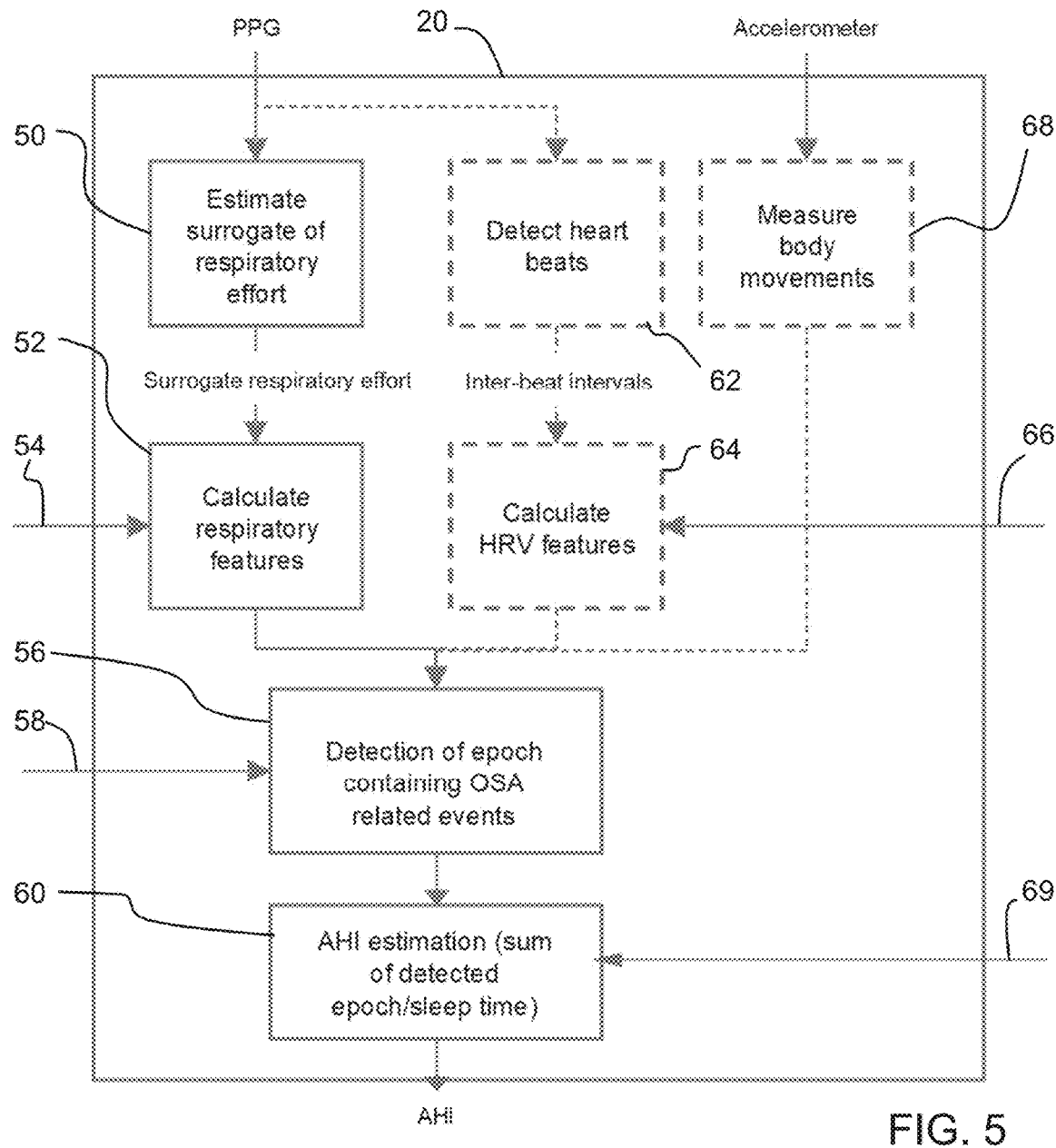
FIG. 5 shows the functions performed by the processor of the system of FIG. 2.

FIG. 5 shows the functions performed by the processor 20. For the purposes of explanation, obstructive apnea events will be discussed, but the same system may detect central apnea events and hypopnea events.

The PPG signal is received as input. In block 50 an estimate or surrogate is made of the respiratory effort and an estimated respiratory effort signal is derived. This signal is provided to a feature extraction unit 52. In this example, the feature extraction unit receives a pre-defined set of respiratory features as input 54.

From these features, epochs containing sleep disordered breathing (apnea or hypopnea) events are detected in block 56. In this example, the block 56 receives a pre-trained classifier as input 58.

An AHI estimation can then take place in block 60.

This processing chain is sufficient to detect the apnea or hypopnea events. However, FIG. 5 shows optional additional processing.

The PPG signal is additionally processed to detect heart beats, in block 62. From this, the inter-beat intervals are determined and the HRV features are calculated in block 64. A pre-defined set of HRV features to be used is for example received as input 66. This HRV information is additionally used in block 56 for detecting the epochs with apnea events.

The accelerometer signal is an additional input to the processor, from which body movements are detected in block 68. This body movement information is additionally used in block 56 for detecting the epochs with apnea events. The movement information can be used to identify and filter out information corrupted by movement artefacts, as well as to extract additional features that can be used to improve the sleep stage classification accuracy. However, the accelerometer in this case does not need to monitor respiration (i.e. chest) movements so may be implemented with the wrist worn PPG sensor.

For estimating the surrogate respiratory effort in block 50, several techniques may be used to extract a respiration surrogate from the PPG signal.

Examples include:

Calculating the amplitude of the PPG pulses (from the start to the peak of the pulse).

Evaluating the respiratory sinus arrhythmia by calculating the distance between PPG pulses.

Computing the envelope of the peaks of the PPG pulses.

It has been shown how to derive a transmissive PPG respiration surrogate in Charlton P. H. et al. "An assessment of algorithms to estimate respiratory rate from the electrocardiogram and photoplethysmogram", Physiol. Meas. 2016; 37 610.

In brief, an example procedure for converting from a PPG signal to a surrogate respiratory effort signal may run as follows.

First, the amplitude ("y-axis") distance between the start and the peak of each PPG pulse is calculated.

Optionally, the amplitude distances determined as being likely influenced by artifacts or arrhythmic heartbeat effects may be removed (e.g. using an algorithm for the estimation of the PPG pulse quality index such as outlined in the paper: Papini, Gabriele B., et al. "Sinus or not: a new beat detection algorithm based on a pulse morphology quality index to extract normal sinus rhythm beats from wrist-worn photoplethysmography recordings." Physiological measurement 39.11 (2018): 115007).

The procedure then further comprises linearly interpolating the amplitude distances to obtain a data series with a fixed (effective) sampling rate, e.g. at 10 Hz.

The interpolated signal is then for example filtered with a band-pass filter between 0.05 Hz (3 breath per minute) and 0.6 Hz (36 breath per minute) in order to remove frequencies that are outside the respiratory range.

Optionally, the procedure may comprise a further step of removing parts of the resulting signal, e.g. by analyzing the average PPG pulse quality (obtained with the algorithm example mentioned above).

The above represents just one example procedure for converting a PPG signal to a surrogate respiration signal. This procedure exploits the changes in blood volume (and therefore in PPG signal amplitude) caused by changes in intrathoracic pressure, which in turn are correlated with the respiratory effort.

Variations on this procedure may be used. For example, instead of using amplitude distances between the start and peak of each pulse, instead the peak-to-trough (maximum to minimum) amplitude differences may be used, or amplitude differences between the point of steepest ascent of the PPG signal and the maximum point of the peak. In some examples, the PPG signal may be pre-processed to compensate for baseline changes in blood volume e.g. by baseline removal, and then amplitude differences between each peak and trough (maximum and minimum) used.

In a further possible variation, instead of amplitude distances, the pulse-width of the PPG pulses may be used instead, these being plotted. The changes in blood volume are also correlated with PPG pulse width though similar mechanisms as for pulse amplitude.

Furthermore, different filtering parameters can be used to those mentioned above, and different exclusion criteria may also be used. For example, in cases where an accelerometer is included next to the PPG sensor, the procedure may involve excluding from the signal derivation signal periods associated with intense movement. Such movement is likely to render the surrogate respiration estimates difficult to determine.

The feature extraction in step 52 may provide automatic detection of apnea and hypopnea events using a set of one more manually engineered features designed to discriminate between apnea and hypopnea events in a surrogate respiratory effort signal.

These features are for example computed in sliding, overlapping windows of e.g. 30-seconds up to 5 minutes, based on the input signal, centered on epochs of e.g. 30-seconds for the complete recording.

Several respiratory features have been shown to be discriminative of sleep and wake, or in general, different sleep stages. Reference is made to Fonseca, Pedro, Xi Long, Mustafa Radha, Reinder Haakma, Ronald M Aarts, and Jérôme Rolink. 2015. "Sleep Stage Classification with ECG and Respiratory Effort." TOP Physiological Measurement 36: 2027-40.

Many respiratory features may be extracted, such as the variance of the respiratory effort signal in the time domain, respiratory frequency and its standard deviation over time periods (such as 150, 210, and 270 s), the mean and standard deviation of breath-by-breath correlation, and the standard deviation in breath length.

Respiratory amplitude features may be used, including the standardized mean, standardized median, and sample entropy of respiratory peaks and troughs (indicating inhalation and exhalation breathing depth, respectively). Other examples include median peak-to-trough difference, median volume and flow rate for a complete breath cycle, inhalation, and exhalation, and inhalation-to-exhalation flow rate ratio.

From the respiratory spectrum, power spectrum density analysis enables the respiratory frequency and its power, the logarithm of the spectral power in different frequency bands; very low frequency, VLF (0.01-0.05 Hz), low frequency, LF (0.05-0.15 Hz), and high frequency, HF (0.15-0.5 Hz), and the LF-to-HF ratio to be used. The modulus and the phase of the pole in the high frequency band may be determined.

Other measures capture the regularity of the signal over different time scales. For example, detrended fluctuation analysis (DFA) is used to identify longer-term correlations in the signal, and sample entropy to quantify the self-similarity of the signal over a given time period.

In more detail, one respiratory feature which is particularly well correlated with sleep disordered breathing events is the standard deviation of the breath duration in the time domain. The breath duration has been found to be statistically different (Mann-Whitney test, p-value<0.05) in approximately 80% of recordings for epochs containing sleep disordered breathing events (hypopnea, obstructive apnea, and mixed apnea events) compared to those with normal breathing. In the case of central apnea events, approximately 90% of recordings have been found to present this statistical difference.

Considering instead the amplitude domain, a further respiratory feature which is particularly well correlated with sleep disordered breathing events is the standardized median of amplitude (see for example the procedure in X. Long et al. "Analyzing respiratory effort amplitude for automated sleep stage classification," Biomed. Signal Process. Control, vol. 14, pp. 197:205, 2014). This feature has been found be statistically different (Mann-Whitney test, p-value<0.05) for approximately 80% of recordings between epochs containing sleep disordered breathing events (hypopnea, obstructive apnea, and central apnea events) and those with normal breathing. In the case of mixed apnea, 100% of the recordings presented this statistical difference.

The reason these features are particularly well correlated with sleep disordered breathing events can be explained as follows.

In the time-domain, the breath duration changes during and after disordered breathing events (when normal breathing is resumed). For instance, the breathing rate is higher, i.e. shorter breath duration, after a respiratory event in order to compensate for the period of absent/reduced airflow.

In the amplitude domain, the standardized median amplitude follows the volumetric decrease generated by the exhalation, therefore it is strongly influenced by those respiratory events that generate a pronounced exhalation, such as breathing resumption after respiratory events. It is known in the literature that the PPG pulse amplitude tends to decrease following arousals (see e.g. C. Karmakar et al. "Detection of Respiratory Arousals Using Photoplethysmography (PPG) Signal in Sleep Apnea Patients," IEEE Journal of Biomedical and Health Informatics, vol. 18, no. 3, pp. 1065-1073, 2014). Since arousals are likely to happen at the end of sleep disordered breathing events, the decrease in amplitude of the PPG pulses is likely to occur at the same time as the decrease in amplitude of a thorax belt signal. Thus the surrogate respiratory effort signal in that case follows a similar pattern to the standard measurement means for respiratory effort.

For the cardiac processing in blocks 62 and 64, several cardiac features have been shown to be useful in monitoring OSA or in general to monitor sleep.

Many features are based on statistics computed over R-R intervals calculated from ECG or on beats detected from PPG measured for example at the wrist, or at the finger-tip.

Features are calculated such as the number of intervals per epoch (expressing the average heart rate in that epoch), the nth percentile, the standard deviation and the range of the interval lengths.

Other features describe characteristics resulting from power spectral density analysis, as mentioned above for the respiratory signal, and from the detrended fluctuation analysis mentioned above.

An additional option is to take account of cardiorespiratory coupling. In addition to analyzing cardiac and respiratory activity separately, cardiorespiratory coupling features express the strength of the coupling between the cardiac and the respiratory autonomic systems, as also discussed in Fonseca et. al. "Sleep Stage Classification with ECG and Respiratory Effort". Features describing cardiorespiratory coupling usually include the phase synchronization between R-R intervals which can be extracted from the PPG signal, and the respiratory phase measured during a number of breathing cycles.

As indicated in FIG. 5, the cardiac and respiratory features can be pre-selected for use by the block 56. Feature selection is for example performed separately during training, for instance, by evaluating the relationship between the presence of an sleep disordered breathing (SDB) event and each of the features on a set of example recordings annotated together with manual scoring based on gold-standard reference PSG. This list can be determined by hand, or more commonly, determined with any of the feature selection algorithms described in literature, such as Correlation Feature Selection. Feature selection is an optional step; the OSA monitoring algorithm can be trained in such a way to learn with which features are more important and in which occasion.

After obtaining the sets of respiratory and cardiac features, the OSA monitoring algorithm can be trained with the example data. In one example, the reference label indicating the presence of a sleep-disordered breathing (SDB)-related event is divided in epochs. Each epoch can have the same duration of the epoch used for the feature calculation. Each reference epoch can consist of a binary label (SDB-related events in the epoch or not) or of a multi-class label (type of SDB-related event in the epoch or no SDB-related events present).

Any classifier described in literature can be used, for example a Logistic Regression can be used to classify epoch containing SDB-related events.

For the apnea-hypopnea index (AHI) estimation in block 60, the number of epochs that are predicted as SDB-related epochs can be divided by the total sleep time in order to obtain the AHI, which is clinically used to determine the OSA severity.

The estimated AHI can be corrected by a correction factor that takes in consideration the maximum amount of SDB-related events that can be present in one epoch. For instance, a 30 second epoch includes on average 1.5 SDB-related events and this would produce an estimated AHI lower than the actual AHI. A multiplicative correction factor of 1.5 to the estimated AHI would correct the estimation.

For example, typically, the recording is divided into non-overlapping epochs of a certain duration, e.g. 30 seconds. In periods of the night when several short SDB events (e.g. 10 seconds each) occur in close succession, it often happens that in a single 30 second epoch multiple SDB events start and finish in the same epoch. If many of these cases occur, a single epoch actually "contains" multiple events. On average, it has been found that each epoch contains 1.5 events. Thus, even for a system that works with 100% accuracy, if one were to compare directly the number of epochs which feature an SDB event with the number of SDB events, one would arrive at a result which is a factor of 1.5 lower. By applying a multiplicative correction factor, this difference can be compensated.

The total sleep time can be obtained for instance by using sleep-staging algorithm based on the PPG signal. A sleep time obtained from PPG based automatic sleep staging can then be provided as input 69. If the total sleep time cannot be calculated, the total duration of the classified epochs can be used as total sleep time surrogate.

In order to evaluate the performance of the system, an epoch-by-epoch classifier was formulated for epochs containing SDB-related events and for determining an AHI. The results were obtained for a set of 108 recordings (the data set not having been used for model training or selection) for a classifier using cardiac (HRV), respiratory effort and body movement features according to the invention, and separately without the use of the respiratory effort features.

The epoch-by-epoch classifier was evaluated in terms of area under the precision-recall curve (PR-AUC) and area under the sensitivity-recall curve (ROC-AUC). The AHI estimation performance was evaluated based on Spearman's correlation between the estimated and the reference AHI and the average absolute AHI error.

The results are described in Table 1, where it can be seen that the classifier has superior performance for both the detection of SDB-related epoch and the AHI estimation.

Table 1 shows the performance comparison between the algorithm trained with HRV and body movements only (HRV+ACT), and the newly trained classifier with respiratory effort and HRV features together with body movements according to the invention.

TABLE 1

|  | HRV + ACT | | RESP + HRV + ACT | |
| --- | --- | --- | --- | --- |
|  | PR-AUC | ROC-AUC | PR-AUC | ROC-AUC |
| SDB epoch detection | 31.6 ± 25.2 | 77.7 ± 11.5 | 33.1 ± 25.4 | 78.9 ± 9.4 |
|  | AHI correlation | AHI abs error | AHI correlation | AHI abs error |
| AHI estimation | 0.5 | 9.7 ± 11.7 | 0.57 | 8.4 ± 10.5 |

There are various additional possible refinements.

As mentioned above, the use of cardiac, and/or cardio-respiratory features is optional but advantageous, since it exploits both the respiratory and cardiac changes that occur together with breathing events. The advantage is that both sets of features (cardiac and respiratory) can be computed from the same base PPG signal without the addition of an extra sensor.

The use of body movements is also optional as mentioned above, but advantageous since some respiratory events are followed by body movements associated with arousals typically following some breathing events. These can be easily measured either from an accelerometer (typically included in most body-worn PPG sensors), or as a surrogate estimate of body movements, computed for example, from body movement artifacts of the actual PPG signal.

In an alternative embodiment, instead of calculating manually engineered respiratory (and optionally) cardiac features, the feature extraction block 52 can be replaced with a deep neural network (e.g. convolutional network) that can be trained directly, together with additional classification layers, to learn optimal representations of the input signals (surrogate respiratory effort from the PPG signal) advantageous for the classification of apnea/hypopnea events.

In an alternative embodiment, instead of calculating the features in discrete, non-overlapping epochs of 30 seconds, the estimation of the likelihood of a breathing event may be calculated e.g. with overlapping windows with a finer resolution, e.g. every 1 second. These estimations are then post-processed to determine intervals with a high likelihood of corresponding to a breathing event. This embodiment has the advantage that the start and duration of each breathing event can be separately estimated, without resorting to the epoch-based representation described above.

A further alternative is the use of deep neural networks, that use as input the raw surrogate respiratory effort, (and optionally a heart rate series, or inter-beat interval series, computed from the PPG signal) and output a likelihood of a breathing event on the same fine resolution of e.g. 1 estimation per second. A similar approach can then be used to estimate the start and end of each breathing event.

As explained above, the breathing events may be used to estimate a surrogate measure of the apnea-hypopnea index (AHI). In the simplest implementation, this estimate is computed as the number of breathing events (or epochs with breathing events) divided by the total recording time. In another embodiment, a sleep/wake classifier based on PPG is used to estimate the total sleep time, and AHI is computed as the number of detected breathing events (or epochs with breathing events) divided by the estimated total sleep time.

In a further refinement, the estimated AHI is derived but additionally with pre-defined thresholds, to estimate the severity of an OSA condition, for example between "no OSA", "mild OSA", "moderate OSA" and "severe OSA". These thresholds can either correspond to those used in clinical practice (e.g. <5, <15, <30 and ≥30 per hour for the 4 categories defined above.

The severity information may instead be customized to maximize the agreement with the traditional classifications using PSG.

Figure 6:
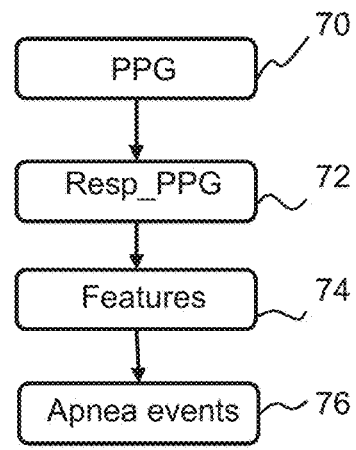
FIG. 6 shows a computer-implemented method for detecting sleep apnea.

FIG. 6 shows a computer-implemented method for detecting sleep apnea, comprising:

in step 70, receiving a PPG signal;

in step 72, providing an estimate of respiratory effort from the PPG signal and thereby deriving a respiratory effort signal;

in step 74 extracting characteristic features from the respiratory effort signal; and in step 76 detecting sleep apnea events from the extracted characteristic features.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for detecting sleep apnea, comprising:
   a PPG sensor for generating a single-wavelength PPG signal for use in detecting sleep apnea; and
   a processor, which is adapted to:
   provide an estimate of respiratory effort from the PPG signal alone and thereby derive a surrogate respiratory effort signal encoded with different and identifiable characteristic features indicative of an occurrence of both sleep disordered breathing events and normal breathing events during sleep, wherein the surrogate respiratory effort signal comprises surrogate feature values that are statistically different between (i) epochs containing an end of a sleep disordered breathing event and (ii) epochs not containing such events, wherein the surrogate feature values provide a surrogate measure of respiratory effort that does not correlate in over 75% of recordings with a conventional measure of respiratory effort, wherein the sleep disordered breathing events include apnea events, hypopnea events, and respiratory-related arousal events;
   extract the characteristic features from the surrogate respiratory effort signal based on a pre-defined set of respiratory features that are statistically different when a sleep ordered breathing event is present; and
   detect sleep disordered breathing events from the extracted characteristic features and thereby distinguish between sleep disordered breathing events and normal breathing during sleep.

2. The system as claimed in claim 1, wherein the processor is adapted to identify epoch periods during which sleep disordered breathing events are detected based upon a pre-trained classifier as input.

3. The system as claimed in claim 1, wherein the processor is adapted to provide an estimate of respiratory effort by one or more of:
   determining the amplitude of pulses in the PPG signal;
   determining the distance between PPG pulses; and
   determining the envelope of the peaks of the PPG pulses.

4. The system as claimed in claim 1, wherein the processor is adapted to extract characteristic features by determining the signal power at the respiration frequency.

5. The system as claimed in claim 1, wherein the processor is further adapted to extract cardiac features from the PPG signal.

6. The system as claimed in claim 5, wherein the processor is adapted to extract cardiac features by one or more of:
   determining the average heart beat interval;
   determining a standard deviation of a heart beat interval;
   determining a range of the heart beat interval; and
   determining the nth percentile of the heart beat interval.

7. The system as claimed in claim 5, wherein the processor is adapted to extract cardiac features by performing power spectral density analysis.

8. The system as claimed in claim 1, wherein the processor is further adapted to extract cardiorespiratory coupling features from the PPG signal.

9. The system as claimed in claim 1, wherein the processor is further adapted to derive sleep stages from heart rate variability information derived from the PPG signal to discriminate between awake and sleep periods.

10. The system as claimed in claim 9, wherein the processor is further adapted to derive an estimated apnea-hypopnea index value based on a total sleep time obtained from the sleep stages and identified epoch periods during which sleep disordered breathing events are detected.

11. The system as claimed in claim 1, wherein the processor is adapted to determine a severity level of the detected sleep disordered breathing events, wherein determining the severity level comprises applying thresholds to apnea-hypopnea index values derived based on a total sleep time obtained from derived sleep stages and identified epoch periods during which sleep disordered breathing events are detected.

12. The system as claimed in claim 1, further comprising an accelerometer for measuring body movements, wherein the processor is adapted to detect sleep disordered breathing events additionally taking account of body movements.

13. The system as claimed in claim 1, wherein the processor is adapted to extract the characteristic features by using a trained neural network.

14. A computer-implemented method for detecting sleep apnea, comprising:
   receiving a single-wavelength PPG signal;
   providing an estimate of respiratory effort from the PPG signal alone and thereby deriving a surrogate respiratory effort signal encoded with different and identifiable characteristic features indicative of an occurrence of both sleep disordered breathing events and normal breathing events during sleep, wherein the surrogate respiratory effort signal comprises surrogate feature values that are statistically different between (i) epochs containing an end of a sleep disordered breathing event and (ii) epochs not containing such events, wherein the surrogate feature values provide a surrogate measure of respiratory effort that does not correlate in over 75% of recordings with a conventional measure of respiratory effort, wherein the sleep disordered breathing events include apnea events, hypopnea events, and respiratory-related arousal events;
   extracting the characteristic features from the surrogate respiratory effort signal based on a pre-defined set of respiratory features that are statistically different when a sleep ordered breathing event is present; and
   detecting sleep disordered breathing events from the extracted characteristic features.

15. A computer program comprising computer program code means which is adapted, when said program is run on a computer, to implement the method of claim 14.

\* \* \* \* \*